United States Patent
Poetsch et al.

(10) Patent No.: US 7,276,633 B2
(45) Date of Patent: Oct. 2, 2007

(54) METHOD FOR PRODUCTION NAPHTHALENE DERIVATIVES

(75) Inventors: Eike Poetsch, Muehltal (DE); Werner Binder, Dieburg (DE); Peer Kirsch, Kanagawa (JP); Andreas Taugerbeck, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 23 days.

(21) Appl. No.: 10/537,307

(22) PCT Filed: Oct. 30, 2003

(86) PCT No.: PCT/EP03/12039

§ 371 (c)(1), (2), (4) Date: Jun. 2, 2005

(87) PCT Pub. No.: WO2004/050594

PCT Pub. Date: Jun. 17, 2004

(65) Prior Publication Data

US 2006/0025615 A1    Feb. 2, 2006

(30) Foreign Application Priority Data

Dec. 3, 2002 (DE) ................................ 102 56 362

(51) Int. Cl.
C07C 41/09 (2006.01)
(52) U.S. Cl. .................. 568/639; 568/649; 568/632; 562/824
(58) Field of Classification Search ................ 568/584, 568/639, 649, 632; 549/20; 562/824
See application file for complete search history.

(56) References Cited

OTHER PUBLICATIONS

John McMurry, Organic Chemistry, 2nd Edition p. 725-726.*

* cited by examiner

*Primary Examiner*—Kamal A. Saeed
*Assistant Examiner*—Yong Chu
(74) *Attorney, Agent, or Firm*—Millen, White, Zelano, Branigan, P.C.

(57) ABSTRACT

The present invention relates to a process for the preparation of a compound of the general formula $$R\text{-}(A^1\text{-}Z\text{-})_m B\text{—}CF_2 O\text{-}A^2\text{-}(A^3)_n\text{—}R' \quad (I)$$

in which

R is alkyl, in which one or more $CH_2$ groups may be replaced, independently of one another, by O, $CF_2$, CH=CH, CH=CF or CF=CF, with the proviso that peroxide structures O—O and formaldehyde acetals O—$CH_2$—O are excluded, $A^1$ is, independently of one another, 1,4-cyclohexylene, 2,5-1,3-dioxanylene, 1,3-cyclobutylene or

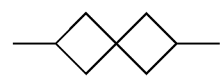

$A^2$ and $A^3$ are 1,4-phenylene, in which, independently of one another, from one to four hydrogens may be replaced by fluorine or one or two CH groups may be replaced by N, Z is a single bond, —$CH_2$—$CH_2$—, —$CF_2$—$CF_2$—, —CH=CH—, —CF=CF—, —CH=CF— or —CF=CH—, B is 2,6-disubstituted naphthalene, 2,6-disubstituted 5,6,7,8-tetrahydronaphthalene or 2,6-disubstituted trans-decalin, R' is R, F, $OCF_3$, $OCF_2H$, $CF_3$, Cl, $SF_5$, CN or NCS, and m and n are, independently of one another, 0 or 1, comprising the following steps:

a) conversion of a compound of the general formula $$R\text{-}(A^1\text{-}Z\text{-})_m BX, \quad (II)$$

in which X is halogen or =O and the other symbols are as defined in relation to the formula (I), into a carboxylic acid derivative with elimination of the group X and introduction of a C1 unit;

b) reaction of the carboxylic acid derivative with a phenol of the general formula $$HO\text{-}A^2(\text{-}A^3)_n\text{—}R', \quad (III)$$

in which $A^2$, $A^3$, R' and n are as defined in relation to the formula (I), to give the compound of the formula (I).

24 Claims, No Drawings

METHOD FOR PRODUCTION NAPHTHALENE DERIVATIVES

The present invention relates to a process for the preparation of liquid-crystalline compounds derived from naphthalene and hydrogenated derivatives of naphthalene and which contain, as characteristic, a —CF$_2$O-bridge in the molecule. The process starts from halogen-substituted naphthalene derivatives, which, after conversion into the corresponding acids, are converted into the target molecules indirectly via the Grignard compounds. This is preferably carried out via the dithioortho esters.

Liquid crystals have found a broad range of applications since the first commercially usable liquid-crystalline compounds were found about 30 years ago. Known areas of application are, for example, displays for watches, pocket calculators and telephones. Further areas of application are displays of portable computers and navigation systems as well as video applications and PC monitors. For the last-mentioned applications in particular, high demands are made of the response times and contrast of the images.

In order to be usable for commercial applications, the liquid-crystalline molecules must have certain properties. In order to be able to employ equipment with a liquid-crystal display under various climatic conditions, the molecules must form a stable nematic phase over the broadest possible temperature range in the region of room temperature. The compounds must thus have a low melting point and a high clearing point.

In order to be able to achieve short response times, the molecules must have low rotational viscosity. Thus, response times of less than 16.7 milliseconds are required for video applications. Furthermore, the liquid-crystalline molecules should have high dielectric anisotropy so that only low threshold voltages are required. This means a low energy requirement, enabling smaller and thus lighter batteries to be used, for example in laptops. Furthermore, the birefringence properties of the molecules, which influence the contrast and the usable viewing angle, are of importance for the design of the display.

In order to be able to satisfy all these requirements simultaneously, use is not made of pure substances, but instead mixtures, which usually comprise from 5 to 15 different components. This means that the individual components must be compatible with one another, i.e., for example, adequately soluble in one another.

For modern active-matrix displays, high contrast of the images is desired. The liquid-crystalline compounds must therefore have high specific resistance and a high voltage holding ratio.

Liquid-crystalline compounds having particularly high specific resistance have proven to be the compounds containing fluorine-containing groups in their molecular structure. Thus, for example, EP 0 844 229 A1 describes liquid-crystalline compounds which contain a CF$_2$O bridge. Various processes have been proposed for the preparation of this bridge. In one of the processes described, an aromatic halide is firstly converted into a Grignard compound or a lithiated compound and is then converted into the dithiocarboxylic acid using carbon disulfide. The dithiocarboxylic acid is converted into a thioester using a phenol in the presence of an alkali metal hydride and iodine. The desired CF$_2$O bridge is then formed using a fluorinating agent.

In another process, it is proposed firstly to react a cyclohexanone with tris(dimethylamino)phosphine and dibromodifluoromethane to give a difluoromethylenehexylidene. Bromine is firstly added onto the latter, and the product is then etherified with formation of a —CF$_2$—O— bridge by reaction with a phenoxide with simultaneous elimination of hydrogen bromide.

Liquid-crystalline naphthalenes, tetralins and decalins have been known for some time (M. Petrzilka, K. Schleich, Helv. Chim. Acta 65, 1982, pages 1242 ff., H. Zollinger et al., Helv. Chem. Acta 64, 1981, pages 1847 ff., and ibid 66, 1983, pages 1574 ff., E. Poetsch, Kontakte 2, 1988, pages 15 ff.).

They have hitherto not been used in liquid-crystal displays in spite of the relatively broad mesophases (W. Schäfer, H. Altmann, H. Zaschke, H. H. Deutscher, Mol. Cryst. Liq. Cryst. 95, 1983, pages 63 ff.) compared with the (commercially used) compounds containing cyclohexyl and phenyl rings, apparently because the increased steric hindrance of the naphthalene structures results in higher flow and rotational viscosity, leading to undesired, extended response times.

Liquid-crystalline compounds which are derived from naphthalene derivatives or (partially) hydrogenated derivatives thereof and contain a CF$_2$O bridge are described in DE 40 06921 A1, JP 2000-1116370/10, JP 1133495, WO 00/10952 A1, JP 2001-19649 and JP 2000-355557. Firstly, however, the cited documents give no indication that the compounds described do not have the usual disadvantages, described above, of liquid-crystalline naphthalene derivatives. Secondly, the cited documents do not disclose an industrially feasible synthesis for the preparation of naphthalene derivatives containing CF$_2$O bridges.

The object of the present invention is therefore the provision of a process of this type. This object is achieved by a process for the preparation of a compound of the general formula $$R-(A^1-Z-)_m B-CF_2 O-A^2-(A^3)_n-R' \quad (I)$$

in which

R is alkyl having from 1 to 12 carbon atoms, preferably having from 1 to 5 carbon atoms and particularly preferably having 1, 3 or 5 carbon atoms, in which one or more CH$_2$ groups may be replaced, independently of one another, by O, CF$_2$, CH=CH, CH=CF or CF=CF, with the proviso that peroxide structures O—O and formaldehyde acetals O—CH$_2$—O are excluded, A$^1$ is, independently of one another, 1,4-cyclohexylene, 2,5-1,3-dioxanylene, 1,3-cyclobutylene or

A$^2$ and A$^3$ are 1,4-phenylene, in which, independently of one another, from one to four hydrogens may be replaced by fluorine or one or two CH groups may be replaced by N, Z is a single bond, —CH$_2$—CH$_2$—, —CF$_2$—CF$_2$—, —CH=CH—, —CF=CF—, —CH=CF— or —CF=CH—, B is 2,6-disubstituted naphthalene, 2,6-disubstituted 5,6,7,8-tetrahydronaphthalene or 2,6-disubstituted trans-decalin, R' is R, F, OCF$_3$, OCF$_2$H, CF$_3$, Cl, SF$_5$, CN or NCS, and m and n are, independently of one another, 0 or 1, comprising the following steps:

a) conversion of a compound of the general formula $$R\text{-}(A^1\text{-}Z\text{-})_m BX \quad (II),$$

in which X is halogen or =O and the other symbols are as defined in relation to the formula (I), into a carboxylic acid derivative with elimination of the group X and introduction of a C1 unit;

b) reaction of the carboxylic acid derivative with a phenol of the general formula $$HO\text{-}A^2(\text{-}A^3)_n\text{—}R' \quad (III),$$

in which $A^2$, $A^3$, R' and n are as defined in relation to the formula (I), to give the compound of the formula (I).

In an embodiment of the present invention, step a) is carried out as follows:

a') conversion of a compound of the general formula $$R\text{-}(A^1\text{-}Z\text{-})_m BX \quad (II),$$

in which X is a halogen and the other symbols are as defined in relation to the formula (I), into the corresponding Grignard compound, reaction of the resultant Grignard compound with $CO_2$, and hydrolysis to the corresponding carboxylic acid of the formula $$R\text{-}(A^1\text{-}Z\text{-})_m B\text{—}CO_2 H \quad (IV)$$

or a salt thereof.

In a further embodiment of the present invention, step a) is carried out as follows:

a") conversion of a compound of the general formula $$R\text{-}(A^1\text{-}Z\text{-})_m BX \quad (II),$$

in which X is an =O group, into a bisalkylthionium salt by reaction with a suitable sulfur-containing compound.

In particular in the case of 2,6-disubstituted trans-decalins, X=O.

In a preferred embodiment of the present invention, X in the formula (II) is selected from the group consisting of Cl, Br and I. X is particularly preferably Br.

The halogen-substituted compounds of the formula (II) are accessible in a manner known per se. They are preferably prepared from the corresponding alcohols by reaction with the corresponding hydrogen halide, thionyl halides or by means of halogen/$PPh_3$. Conversion of the compounds of the formula (II) into the corresponding Grignard compound is possible in the manner described in DE 102 20 549 A1, which relates to the preparation of decalin derivatives. Owing to their configurative instability, the resultant Grignard compounds of the decalin derivatives have an all-trans configuration, i.e. both an axial halide and an equatorial halide give an equatorial MgBr derivative. This stereochemistry is also retained in the subsequent acids (IV) or the reaction products formed therefrom. The process disclosed in DE 102 20 549 A1 for the preparation of Grignard compounds is an integral constituent of the present application and is incorporated herein by way of reference.

The process for the preparation of the Grignard compounds is described briefly again below since it is employed in the present invention not only for the preparation of the corresponding 2,6-decalin derivatives, but also for the preparation of the 2,6-tetrahydronaphthalene and 2,6-naphthalene derivatives.

To this end, a compound of the formula (II) in which B=2,6-decalinyl, 2,6-tetrahydronaphthyl or 2,6-naphthyl and X=halogen is reacted with magnesium in a solvent which comprises at least one nonpolar solvent and at least one polar solvent, with external supply of heat.

It is particularly advantageous that the desired Grignard reaction in accordance with the invention proceeds without or with only a small proportion of beta-elimination resulting, for example, in the formation of HBr or HMgBr.

Examples of suitable nonpolar solvents are aliphatic and aromatic hydrocarbons containing no polar groups, for example hexane, cyclo-hexane, benzene, toluene or xylene, or mixtures of these solvents.

Suitable polar solvents are, for example, ethers, such as, for example, diethyl ether, methyl tert-butyl ether, dimethoxyethane, tetrahydrofuran or dioxane.

The mixing ratio (based on volumes) of the nonpolar solvent or mixture to the polar solvent or mixture is generally from 10:1 to 1:2, preferably from 8:1 to 1:1 and particularly preferably from 6:1 to 2:1.

A particularly preferred solvent mixture is benzene and/or toluene with tetrahydrofuran. A mixing ratio of from 5:1 to 3:1 is advantageously selected here.

Besides the solvent mixtures having two components, those having 3, 4, 5 or more components can also be employed so long as in each case at least one adequately polar solvent and in each case at least one essentially nonpolar solvent are present.

The reaction is advantageously carried out at the boiling point of the solvent mixture under atmospheric pressure. A preferred temperature range is from 40 to 100° C. and particularly preferably from 50 to 80° C.

In a preferred embodiment, magnesium in a suitable form, for example in the form of turnings, is initially introduced in a protective-gas atmosphere, for example nitrogen, and some of the solution comprising the halogen compound of the formula (II) is added. The amount initially introduced in this way is, in accordance with the invention, warmed with the magnesium, and a suitable initiator, for example iodine or a small amount of dibromoethane, is added. After the reaction has commenced, the majority of the solution is added over a period, which can be up to 120 minutes, and the reaction mixture is warmed for a further 5 to 360 minutes, preferably under reflux. Only after complete addition and ongoing external supply of heat does the majority of the magnesium react, with the requisite time for external supply of heat generally being longer than the previous addition time of the solution. The external supply of heat is provided in accordance with the invention in order to maintain the reaction since the formation of the Grignard compound is not sufficiently exothermic.

After cooling, the Grignard compound is separated off and purified in a manner known to the person skilled in the art; the subsequent reaction is preferably carried out using the reaction solution obtained.

The Grignard compound obtained is subsequently reacted with $CO_2$. The stereochemistry of the molecule is retained here (cf. scheme I, which applies both to decalin and tetrahydronaphthalene derivatives). Naphthalene-, tetrahydronaphthalene- and decalincarboxylic acid derivatives are generally prepared without prior isolation of the Grignard compound, i.e. the Grignard compound is formed in situ and reacted directly with $CO_2$. The same solvents mentioned above in connection with the preparation of the Grignard compound are thus used.

Scheme (I)

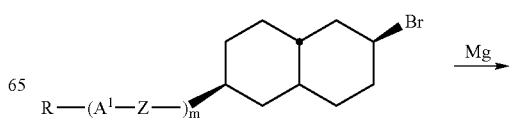

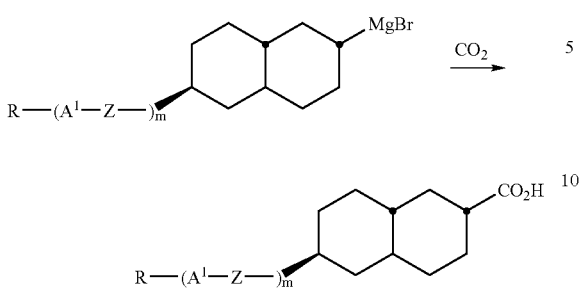

In order to avoid decomposition of the Grignard reagent by a Zerewitinoff reaction, caused by condensed water contamination on the surface of the dry ice, gaseous $CO_2$ is preferably employed.

After completion of the reaction, the carboxylic acid is liberated by hydrolysis. The carboxylic acid or the salt is then isolated in a manner known per se.

The target compound containing a —$CF_2O$— bridge is subsequently formed from the carboxylic acid. There are various possibilities for doing this, some of which proceed via the corresponding esters.

In one embodiment, the esters are formed from the acids (IV) and the phenols of the formula (III) HO-$A^2$(-$A^3$)$_n$—R', in which $A^2$, $A^3$, R' and n are as defined in relation to the formula (I), with the starting materials being reacted with one another under water-eliminating conditions. In many cases, a water-eliminating substance is used, for example cyclohexylcarbodiimide, or the acid halide prepared by means of a mixed inorganic acid anhydride ($SOCl_2$, $PCl_3$, $POCl_3$ or $PBr_3$) is converted into the corresponding ester in the presence of a base (pyridine, 4-dimethylaminopyridine or triethylamine).

The reaction is preferably carried out in the presence of cyclohexylcarbodiimide under conditions known to the person skilled in the art.

After the preparation of the esters, the latter are converted into the desired compounds of the formula (I) under conditions known per se.

Preferred methods include sulfuration using Lawesson's reagent (2,4-bis(4-methoxyphenyl)-1,2,3,4-dithiadiphosphetane-2,4-dithione) with formation of the thioesters as intermediates, followed by oxidative fluorodesulfuration, with the desulfuration preferably being carried out using a brominating agent.

Examples of suitable fluorinating agents include aliphatic and aromatic amine/hydrogen fluoride complexes, pyridine/hydrogen fluoride complexes, $NEt_3$.3HF, 50% HF in pyridine, melamine.HF and polyvinylpyridine.HF.

Examples of suitable oxidants/brominating agents include compounds which liberate halonium equivalents, preferably from the group consisting of dibromohydantoin, dimethyldibromohydantoin, N-bromosuccinimide, N-iodosuccinimide, 1,3-dibromo-5,5-dimethylhydantoin, $SO_2Cl_2$, $SO_2ClF$, nitrosonium and nitronium salts, chloramine T and bromine, particularly preferably bromine.

For the above-mentioned preparation processes, reference is made, for example, to T. Hiyama et al., Bull. Chem. Soc. Jpn. 73, 2000, 1875; and Tetrahedron Letters 33, 1992, 4173.

The most preferred method for the preparation of the ethers (I) from the acids (IV) is conversion into the bis (alkylthio)carbenium salts (V) and conversion thereof into the desired compounds of the formula (I) by reaction with the phenols of the formula (III) in the presence of a fluorinating agent and an oxidant.

The process is depicted in the following scheme (II).

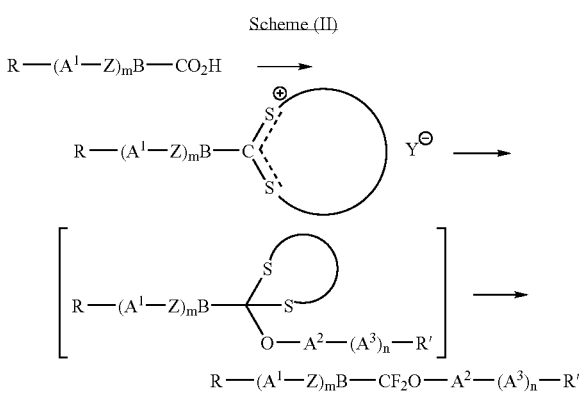

In this process, the carboxylic acid (IV) is reacted with an alkylthiol to give the bis(alkylthio)carbenium salt (V). Instead of a carboxylic acid, it is also possible to employ a carboxylic acid derivative in which halogen, pseudo-halogen, substituted sulfonate, alkoxy or phenoxy is present instead of the —OH group, or an anhydride. However, this is not preferred since this would comprise a further reaction step.

Preference is given to the use of thiols which result in the formation of a cyclic cation. Ethanedithiol, propanedithiol and 1,2-benzenedithiol, which result in the formation of dithianylium or dithiolanylium salts, are particularly suitable. The salt (V) is subsequently reacted with a phenol (III) to give the orthoester (VI). This is generally not isolated, but instead converted directly into the ether (I) by oxidative fluorination. The above-described process for the preparation of the ethers (I) is described in WO 01/64667. This process is an integral constituent of the present application and is incorporated herein by way of reference.

In an alternative embodiment of the present invention, the bisalkylthionium salt is obtained starting from a keto compound of the formula (II) in which X is an =O group and B is a decalinyl radical. This preparation is carried out in a manner known per se. Reference may be made here by way of example to D. J. Ager, Org. React. 38, 1990, pages 1 to 223, in particular pages 63, 95 and 96. In this process, ketones are added to the deprotonated 2-silyl-1,3-dithiane and, after warming at room temperature for 15 to 90 minutes, are optionally held at this temperature for a further 90 minutes. After conventional work-up with addition of $NH_4Cl$ solution, ketene dithioketals are thus obtained and are subsequently converted into the bisalkylthionium salts. This is generally carried out by acidification. The resultant salt is then reacted with the phenol (III) in the presence of a fluorinating agent and oxidant to give the compound (I). A process which is preferred in accordance with the invention for the preparation of the ketene dithioketals is reaction with a 2-silyl-1,3-dithiane, which may be optionally substituted. Particular preference is given to the use of 2-trimethylsilyl-1,3-dithiane. The reaction is preferably carried out in the presence of a deprotonating compound, for example alkyllithium, preferably n-butyllithium. The reaction temperature is preferably at values of from −130 to 0° C., particularly preferably from −35 to 0° C. Preferred solvents are selected from the group consisting of the ethers and haloalkanes, for example diethyl ether, tetrahydrofuran or dichloromethane, or mixtures thereof.

The process for the preparation of bis(alkylthio)carbenium salts and conversion into compounds containing a $CF_2O$ bridge is described in DE 101 05313 A1. The part of DE 101 05313 A1 relating to this process is an integral constituent of the present invention and is incorporated herein by way of reference.

The acid employed for the protonation of the ketene dithioketal is one of the general formula $H^+Y^-$, where $Y^-$ is a non-coordinating or weakly coordinating anion. $Y^-$ is preferably selected from the group consisting of halides, tetrafluoroborate, hexafluorophosphate, perchlorate, alkylcarbonate, arylcarbonate, alkylsulfonate and arylsulfonate. One, a plurality of or all the H atoms in the alkyl and aryl groups here may be substituted by fluorine or chlorine. Particularly preferred acids are trifluoromethanesulfonic acid and tetrafluoroboric acid/diethyl ether complex.

The acid is employed in an approximately equimolar amount based on the ketene dithioketal units to be reacted. The reaction is advantageously carried out at a temperature in the range from −80 to +30° C. in an inert polar solvent or solvent mixture. Suitable solvents are, for example, ethers and haloalkanes and mixtures thereof, for example diethyl ether, tetrahydrofuran or dichloromethane.

The bis(alkylthio)carbenium salt preferably has a non-coordinating or weakly coordinating anion, which is particularly preferably selected from the group formed by tetrafluoroborate, hexafluorophosphate, perchlorate and perfluoroalkylsulfonate, in particular trifluoromethanesulfonate. These salts are simple to use since they are virtually non-hygroscopic.

In the reaction of the bis(alkylthio)carbenium salts with the phenols (III), the oxidants used can be conventional oxidants. The oxidant employed is preferably a compound which liberates halonium equivalents. Illustrative oxidants are dimethyidibromohydantoin, N-bromosuccinimide, N-iodosuccinimide, 1,3-dibromo-5,5-dimethylhydantoin and bromine. Particular preference is given to bromine, since the resultant bromides can easily be separated off. Likewise suitable are, for example, $SO_2Cl_2$, $SO_2ClF$, nitrosonium and nitronium salts as well as chloramine T.

Fluorinating agents which can be employed are conventional fluorinating agents. The fluorinating agent is particularly preferably selected from the group formed by aliphatic and aromatic amine/hydrogen fluoride complexes, pyridine/hydrogen fluoride complexes, $NEt_3.3HF$, 50% HF in pyridine, melamine.HF and polyvinylpyridine.HF.

The invention is explained in the following, non-restricting examples.

EXAMPLE 1

Preparation of 6β-propyl-(4aα,8aβ)-decahydronaphthalene-2α-carboxylic acid

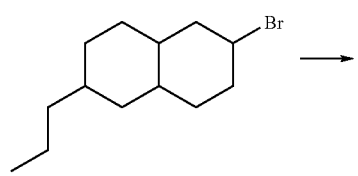

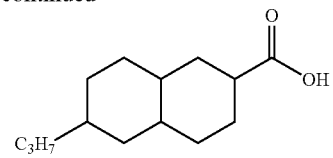

10.0 g (0.4111 mol) of magnesium turnings were initially introduced, and a solution of 100.0 g (0.386 mol) of n-propyl-cis-decalinyl bromide (2β-bromo-6β-propyl-(4aα,8aβ)-decahydronaphthalene) in 770 ml of a 4:1 mixture of benzene and tetrahydrofuran was subsequently added at the boiling point. When the addition was complete, the mixture was refluxed for a further 30 minutes and subsequently cooled to −10° C. $CO_2$ (obtained by evaporation of dry ice) was then passed in. The temperature rose to 15° C. When the reaction was complete, water was added, and the mixture was acidified using HCl and diluted with 600 ml of methyl tert-butyl ether. The organic phase was separated off and evaporated in a rotary evaporator. The crude product obtained was recrystallised from heptane, giving 36.4 g (41.9%) of the product as crystals in a purity of 99.6%.

EXAMPLE 2

Preparation of 2-(6β-propyl-(4aα,8aβ)-decahydronaphthalene-2α-yl)-1,3-dithian-2-ylium trifluoromethanesulfonate

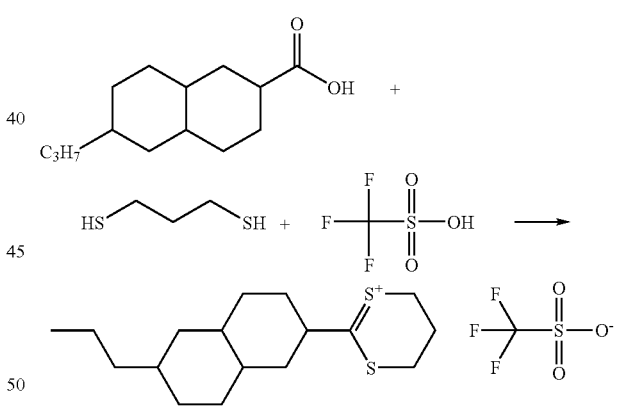

15.4 g (0.069 mol) of the acid obtained in Example 1 were reacted with 6.915 ml (0.069 mol) of 1,3-propanedithiol and 15.6 ml (0.177 mol) of trifluoromethanesulfonic acid by initially introducing the acid and the thiol and adding the trifluoromethanesulfonic acid dropwise. When the slightly exothermic reaction was complete, the mixture was stirred at 120° C. for 75 minutes. After the mixture had been cooled to about 80° C., 42 ml of dibutyl ether were added. After a further 100 ml of dibutyl ether had been added, the solution was stored overnight at −20° C., giving 49.2 g of an oil, which was employed as such in the next step. The content of dithianylium salt was estimated at 50%. Digestion with diethyl ether at −80° C. gives 21.9 g of crystals from the oil obtained in a repetition batch.

EXAMPLE 3

Preparation of 2α-[(difluoro-3,4,5-trifluorophenoxy) methyl]-6β-propyl-(4aα,8aβ)-decahydronaphthalene

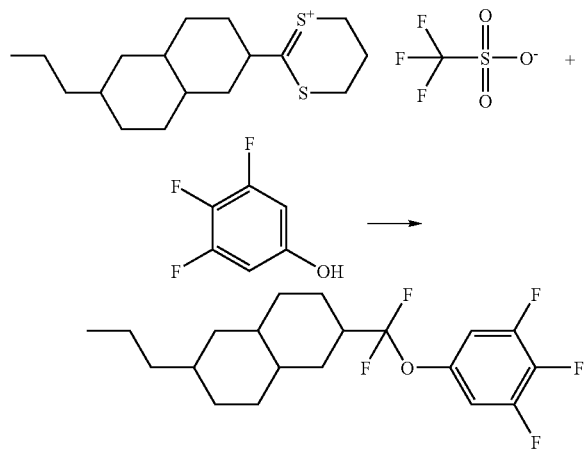

49.2 g (0.035 mol) of the product obtained in Example 2 having an assumed content of 50% were initially introduced in 300 ml of dichloromethane at −70° C., and a mixture of 23.1 ml (0.166 mol) of triethylamine and 8.75 g (0.053 mol) of 3,4,5-trifluorophenol in 100 ml of dichloromethane was added dropwise at this temperature. A colourless solid temporarily precipitated and re-dissolved at the end. The mixture was allowed to stir at −70° C. for 1.5 hours, 29.75 ml of triethylamine trishydrofluoride were subsequently added dropwise at this temperature, the mixture was allowed to stir for a further 30 minutes, and 48.608 g (0.170 mol) of 1,3-dibromo-5,5-dimethylhydantoin were subsequently added. After a further 1.5 hours, the batch was allowed to warm to 0° C. The yellow suspension was subsequently carefully added to NaCO₃ solution with stirring. The organic phase was separated off, and the aqueous phase was again extracted with dichloromethane. The combined organic phases were again washed with saturated sodium hydrogencarbonate solution and water, and the solvent was removed under reduced pressure. After double filtration through silica gel, the product was recrystallised, giving 7.5 g (36.2%) of product.

EXAMPLE 4

Preparation of 2-[(difluoro-3,4,5-trifluorophenoxy) methyl]-6-ethylnaphthalene

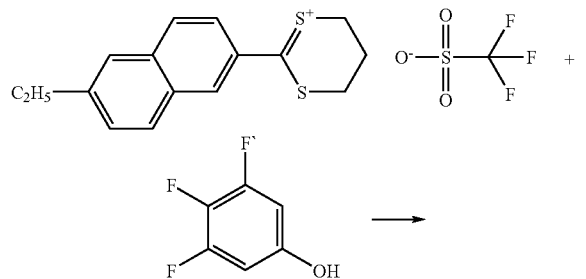

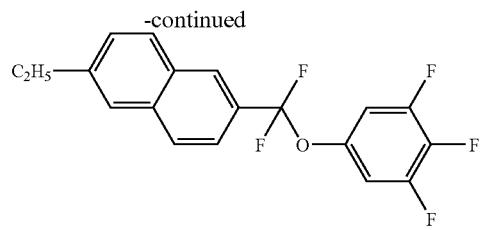

22.5 g (0.053 mol) of 2-(6-ethylnaphth-2-yl)-1,3-dithian-2-ylium trifluoromethanesulfonate were initially introduced in 440 ml of dichloromethane at −70° C., and a mixture of 12.689 ml (0.090 mol) of triethylamine and 7.85 g (0.053 mol) of 3,4,5-trifluorophenol in 640 ml of dichloromethane was added dropwise at this temperature. A colourless solid temporarily precipitated and re-dissolved at the end. The mixture was allowed to stir at −70° C. for 1.5 hours, 44.942 ml of triethylamine trishydrofluoride were subsequently added dropwise at this temperature, the mixture was allowed to stir for a further 30 minutes, and 73.65 g (0.257 mol) of 1,3-dibromo-5,5-dimethylhydantoin were subsequently added. After a further 1.5 hours, the batch was allowed to warm to 0° C. The yellow suspension was subsequently carefully added to NaHCO₃ solution with stirring. The organic phase was separated off, and the aqueous phase was again extracted with dichloromethane. The combined organic phases were again washed with saturated sodium hydrogencarbonate solution and water, and the solvent was removed under reduced pressure. After filtration through silica gel and chromatography over silica gel with heptane/toluene (9:1), the product was recrystallised, giving 1.9 g (10.1%) of product.

The starting material, 2-(6-ethylnaphth-2-yl)-1,3-dithian-2-ylium trifluoromethanesulfonate, was obtained from 6-ethylnaphthalene-2-carboxylic acid in an analogous manner to that described in Examples 1 and 2.

EXAMPLE 5

Preparation of 2-[(difluoro-(3,5-difluoro-4-trifluoromethoxy)phenoxy)-methyl]-6-ethylnaphthalene

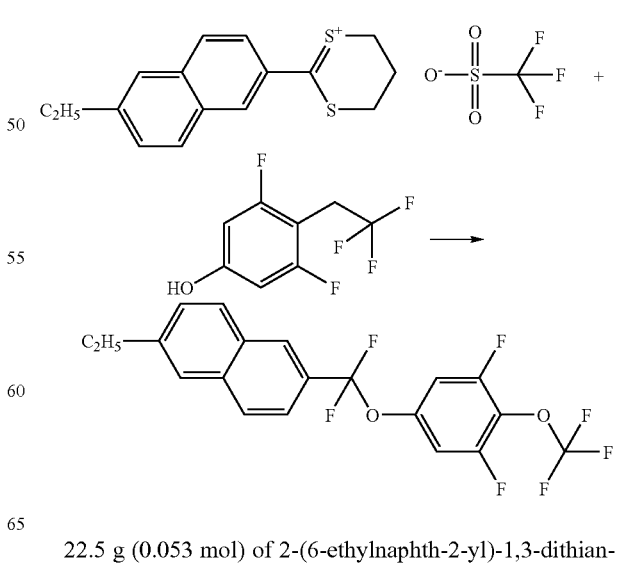

22.5 g (0.053 mol) of 2-(6-ethylnaphth-2-yl)-1,3-dithian-2-ylium trifluoromethanesulfonate were initially introduced in 440 ml of dichloromethane at −70° C., and a mixture of 12.69 ml (0.090 mol) of triethylamine and 13.349 g (0.053 mol) of 3,5-difluoro-4-(trifluoromethoxy)phenol in 200 ml of dichloromethane was added dropwise at this temperature. A colourless solid temporarily precipitated and re-dissolved at the end. The mixture was allowed to stir at −70° C. for 1.5 hours, 44.942 ml of triethylamine trishydrofluoride were subsequently added dropwise at this temperature, the mixture was allowed to stir for a further 30 minutes, and 73.65 g (0.257 mol) of 1,3-dibromo-5,5-dimethylhydantoin were subsequently added. After a further 1.5 hours, the batch was allowed to warm to 0° C. The yellow suspension was subsequently carefully added to NaHCO₃ solution with stirring. The organic phase was separated off, and the aqueous phase was again extracted with dichloromethane. The combined organic phases were again washed with saturated sodium hydrogencarbonate solution and water, and the solvent was removed under reduced pressure. After filtration through silica gel, the product was recrystallised, giving 5.2 g (23.3%) of product.

EXAMPLE 6

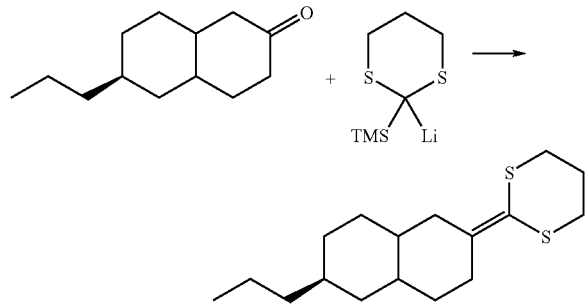

50.0 g (0.260 mol) of 2-trimethylsilyl-1,3-dithiane were dissolved in 900 ml of THF, and 167 ml (0.273 mol) of a 15% solution of n-butyllithium in hexane were added dropwise at −70° C. The batch was allowed to thaw gradually to 0° C. over the course of 4 hours and was re-cooled to −70° C., and a solution of 50.0 g (0.260 mol) of 6-n-propyl-trans-decalin-2-one in 100 ml of THF was subsequently added dropwise. When the addition was complete, the cooling was removed, and the clear yellow solution was allowed to stir overnight. The batch was subsequently introduced into 1000 ml of ice-water, and the aqueous phase was separated off and extracted three times with 300 ml of petroleum ether each time. The combined organic phases were washed twice with saturated sodium chloride solution and dried over sodium sulfate. The solvent was removed under reduced pressure, and the crude product was recrystallised from n-heptane, giving 63.2 g (82%) of 2-(6β-propyl-(4aα,8aβ)-decahydronaphth-2-ylidene-1,3-dithiane as a colourless solid.

EXAMPLE 7

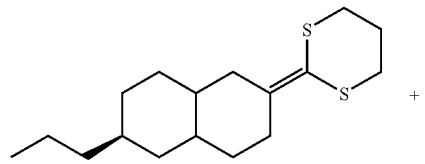

+

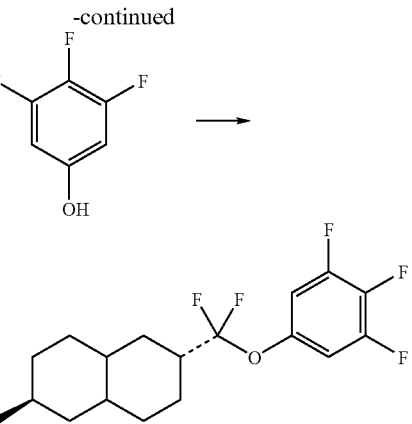

50.0 g (0.169 mol) of 2-(6β-propyl-(4aα,8aβ)-decahydronaphth-2-ylidene-1,3-dithiane were dissolved in 200 ml of dichloromethane, and 14.8 ml (0.169 mol) of trifluoromethanesulfonic acid were added carefully with ice-cooling. After 15 minutes, the cooling was removed, and the mixture was stirred at room temperature for a further 30 minutes. The batch was subsequently cooled to −70° C., a mixture of 42.3 ml (0.304 mol) of triethylamine and 37.5 g (0.254 mol) of 3,4,5-trifluorophenol in 100 ml of dichloromethane was added, and the mixture was stirred at −70° C. for 1 hour. 136 ml (0.845 mol) of triethylamine trishydrofluoride were then added to the solution, and, after 5 minutes, a suspension of 242 g (0.845 mol) of 1,3-dibromo-5,5-dimethylhydantoin in 300 ml of dichloromethane was added in portions over the course of 30 minutes. The mixture was allowed to stir for a further 60 minutes, the batch was allowed to thaw to −20° C., and the orange solution was added to 1 l of ice-cold 1 M sodium hydroxide solution with stirring. The organic phase was separated off, and the aqueous phase was extracted three times with dichloromethane. The combined organic phases were washed twice with saturated sodium chloride solution and dried over sodium sulfate. After removal of the solvent under reduced pressure, the residue was filtered through silica gel with n-hexane, and the crude product was recrystallised from n-hexane, giving 55.3 g (87%) of 2α-[(difluoro-3,4,5-trifluorophenoxy)methyl]-6β-propyl-(4aα,8aβ)-decahydronaphthalene as colourless crystals (melting point: 56° C.).

What is claimed is:

1. A process for preparing a compound of formula (I)

$$R\text{-}(A^1\text{-}Z\text{-})_m, B\text{---}CF_2O\text{-}A^2\text{-}(A^3)_n\text{---}R' \qquad (I)$$

in which

R is alkyl, in which one or more $CH_2$ groups are optionally replaced, independently of one another, by O, $CF_2$, CH=CH, CH=CF or CF=CF, with the proviso that peroxide structures O—O and formaldehyde acetals O—$CH_2$—O are excluded, $A^1$ is, independently of one another, 1,4-cyclohexylene, 2,5-1,3-dioxanylene, 1,3-cyclobutylene or

$A^2$ and $A^3$ are 1,4-phenylene, in which, independently of one another, from one to four hydrogens are optionally replaced by fluorine or one or two CH groups are optionally replaced by N, Z is a single bond, —$CH_2$—$CH_2$—, —$CF_2$—$CF_2$—, —CH=CH—, —CF=CF—, —CH=CF— or —CF=CH—, B is 2,6-disubstituted trans-decalin, R' is R, F, $OCF_3$, $OCF_2H$, $CF_3$, Cl, $SF_5$, CN or NCS, and m and n are, independently of one another, 0 or 1, said process comprising the following steps:

a) converting a compound of formula (II)

$$R\text{-}(A^1\text{-}Z\text{-})_m BX \qquad (II),$$

in which X is halogen or =O, into a carboxylic acid or a salt of a carboxylic acid with elimination of the group X; and b) converting said carboxylic acid or salt of a carboxylic acid using a phenol of formula (III)

$$HO\text{-}A^2(\text{-}A^3)_n\text{—}R' \qquad (III),$$

to obtain a compound of formula (I).

2. A process according to claim 1, wherein said compound of formula (II) is converted into a carboxylic acid of the formula (IV), $R\text{-}(A^1\text{-}Z\text{-})_m B\text{—}CO_2H$ (IV), or a salt thereof, and step a) is carried out as follows:

a') a compound of formula (II)

$$R\text{-}(A^1\text{-}Z\text{-})_m BX \qquad (II),$$

in which X is a halogen, is converted into the corresponding Grignard compound, reacting the resultant Grignard compound with $CO_2$, and hydrolysing the resultant compound to form the corresponding carboxylic acid of formula (IV)

$$R\text{-}(A^1\text{-}Z\text{-})_m B\text{—}CO_2H \qquad (IV)$$

or a salt thereof.

3. A process according to claim 1, wherein X in formula (II) is selected from the group consisting of Cl, Br and I.

4. A process according to claim 1, wherein the reaction of the Grignard compound with $CO_2$ is carried out using gaseous $CO_2$.

5. A process according to claim 2, wherein in the conversion of the carboxylic acid of formula (IV) using a phenol of formula (III), an ester is obtained by reaction under water-eliminating conditions, and said ester is subsequently converted into an ether compound of formula (I).

6. A process according to claim 5, wherein said ether of formula (I) is obtained by conversion of said ester by oxidative fluorodesulfuration.

7. A process according to claim 1, wherein said carboxylic acid or salt of said carboxylic acid is a bis(alkylthio) carbenium salt which is obtained by reacting a carboxylic acid of formula (IV)

$$R\text{-}(A^1\text{-}Z\text{-})_m B\text{—}CO_2H \qquad (IV)$$

with an alkylthiol to obtain said bis(alkylthio)carbenium salt, said bis(alkylthio)carbenium salt is then reacted with said phenol of formula (III) to form an orthoester, and said orthoester is converted to an ether of formula (I) by oxidative fluorination using an oxidant.

8. A process according to claim 6, the oxidant employed in the oxidative fluorodesulfuration is a compound which liberates halonium.

9. A process according to claim 6, wherein the fluorinating agent employed in the oxidative fluorodesulfuration is selected from aliphatic and aromatic amine/hydrogen fluoride complexes, pyridine/hydrogen fluoride complexes, $NEt_3.3HF$, 50% HF in pyridine, melamine.HF and polyvinylpyridine.HF.

10. A process according to claim 5, wherein said ester is reacted with a fluorinating agent in the presence of an oxidant to give an ether of formula (I) with formation of a thioester as an intermediate.

11. A process according to claim 1, wherein said carboxylic acid or salt of said carboxylic acid is a bis(alkylthio) carbenium salt and step a) is carried out as follows:

a") a compound of formula (II)

$$R\text{-}(A^1\text{-}Z\text{-})_m BX \qquad (II),$$

in which X is an =O group, is converted into a bis (alkylthio)carbenium salt by reaction with a suitable sulfur-containing compound.

12. A process according to claim 11, wherein a compound of formula (II) is reacted with an optionally substituted 2-silyl-1,3-dithiane in the presence of a deprotonating compound to obtain a ketene dithioketal which is subsequently converted into said bis(alkylthio)carbenium salt.

13. A process according to claim 12, said ketene dithioketal is converted into said bis(alkylthio)carbenium salt by acidification and the acid employed for protonation of said ketene dithioketal is of the formula $H^+Y^-$.

14. A process according to claim 11, wherein said bis (alkylthio)carbenium salt has a non-coordinating or weakly coordinating anion selected from tetrafluoroborate, hexafluorophosphate, perchlorate and perfluoroalkylsulfonate.

15. A process according to claim 11, wherein said bis (alkylthio)carbenium salt is reacted with said phenol of formula (III) in the presence of an oxidant and a fluorinating agent, and said oxidant is a compound which liberates halonium.

16. A process according to claim 11, wherein said bis (alkylthio)carbenium salt is reacted with said phenol of formula (III) in the presence of an oxidant and a fluorinating agent, and said fluorinating agent is selected from aliphatic and aromatic amine/hydrogen fluoride complexes, pyridine/hydrogen fluoride complexes, $NEt_3.3HF$, 50% HF in pyridine, melaminee.HF and polyvinylpyridine.HF.

17. A process according to claim 3, wherein X in formula (II) is Br.

18. A process according to claim 7, wherein said alkylthiol is a cyclic alkylthiol.

19. A process according to claim 7, wherein said alkylthiol is ethanedithiol, propanedithiol or 1,2-benzenedithiol.

20. A process according to claim 8, wherein said compound which liberates halonium is selected from the group consisting of dibromohydantoin, dimethyldibromohydantoin, N-bromosuccinimide, N-iodosuccinimide, 1,3-dibromo-5,5-dimethylhydantoin, $SO_2Cl_2$, $SO_2ClF$, nitrosonium and nitronium salts, chloramine T and bromine.

21. A process according to claim 10, wherein the oxidant is a brominating agent.

22. A process according to claim 15, wherein said compound which liberates halonium is selected from the group consisting of dibromohydantoin, dimethyldibromohydantoin, N-bromosuccinimide, N-iodosuccinimide, 1,3-dibromo-5,5-dimethylhydantoin, $SO_2C_2$, $SO_2ClF$, nitrosonium and nitronium salts, chloramine T and bromine.

23. A process according to claim 1, wherein $A^1$ is 1,4-cyclohexylene, 2,5-1,3-dioxanylene, or 1,3-cyclobutylene.

24. A process according to claim 1, wherein m and n are each 0.

* * * * *

UNITED STATES PATENT AND TRADEMARK OFFICE
CERTIFICATE OF CORRECTION

PATENT NO. : 7,276,633 B2
APPLICATION NO. : 10/537307
DATED : October 2, 2007
INVENTOR(S) : Eike Poetsch It is certified that error appears in the above-identified patent and that said Letters Patent is hereby corrected as shown below:

Column 12, line 52, in formula (I), reads "R-(A$^1$-Z-)$_m$, B-..." should read
-- R-(A$^1$-Z-)$_m$B-... --
Column 13, line 10, begin new line after "0 or 1,"
Column 13, line 30, reads "halogen, is" should read -- halogen, which is --
Column 13, line 62, reads "claim 6, the" should read -- claim 6, wherein the --
Column 14, line 22, reads "claim 12, said" should read -- claim 12, wherein said --
Column 14, lines 28-29, reads "tetrafi uoroborate, hexafi uorophosphate," should read
-- tetrafluoroborate, hexafluorophosphate, --
Column 14, line 41, reads "melaminee.HF" should read -- melamine.HF --
Column 14, line 53, reads "chioramine T" should read -- chloramines T --
Column 14, line 60, reads "SO$_2$C$_2$," should read -- SO$_2$Cl$_2$, --

Signed and Sealed this

Nineteenth Day of August, 2008

JON W. DUDAS
*Director of the United States Patent and Trademark Office*